(12) United States Patent
Hwang et al.

(10) Patent No.: US 8,334,060 B2
(45) Date of Patent: Dec. 18, 2012

(54) TRIARYLAMINE-BASED COMPOUND, METHOD OF PREPARING THE SAME, AND ORGANIC LIGHT EMITTING DEVICE USING THE TRIARYLAMINE-BASED COMPOUND

(75) Inventors: Seok-Hwan Hwang, Suwon-si (KR); Young-Kook Kim, Suwon-si (KR); Chang-Ho Lee, Suwon-si (KR); Seok-Jong Lee, Suwon-si (KR); Seung-Gak Yang, Suwon-si (KR); Hee-Yeon Kim, Suwon-si (KR); Jung-Han Shin, Suwon-si (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 206 days.

(21) Appl. No.: 12/453,211

(22) Filed: May 1, 2009

(65) Prior Publication Data
US 2009/0278451 A1    Nov. 12, 2009

Related U.S. Application Data

(62) Division of application No. 11/489,565, filed on Jul. 20, 2006, now abandoned.

(30) Foreign Application Priority Data

Jul. 22, 2005  (KR) .................. 10-2005-0066959

(51) Int. Cl.
*H01L 51/54*    (2006.01)
*C07C 211/00*   (2006.01)

(52) U.S. Cl. ........ 428/690; 428/917; 313/504; 313/506; 564/307

(58) Field of Classification Search ......................... None
See application file for complete search history.

(56) References Cited

U.S. PATENT DOCUMENTS
4,933,245 A    6/1990   Akasaki et al.
(Continued)

FOREIGN PATENT DOCUMENTS
DE    19619484    11/1996
(Continued)

OTHER PUBLICATIONS

Machine translation for JP 2004-047442, which was published Feb. 2004.*

(Continued)

*Primary Examiner* — Dawn L. Garrett
(74) *Attorney, Agent, or Firm* — Robert E. Bushnell, Esq.

(57) ABSTRACT

A triarylamine-based compound of formula 1, a method of preparing the same, and an organic light emitting device including the triarylamine-based compound of formula 1:

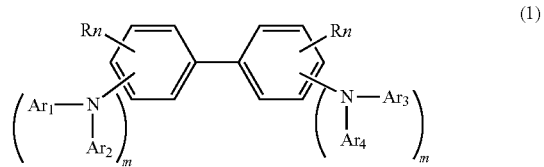

where $Ar_1$ through $Ar_4$ are independently a substituted or unsubstituted C6-C30 aryl group or a substituted or unsubstituted C2-C30 heterocyclic group; R is a halogen atom, a cyano group, a substituted or unsubstituted C1-C30 alkyl group; n is an integer of 1 through 3; and m is an integer of 1 through 3. The triarylamine-based compound of formula 1 has excellent electrical properties and a great charge transporting capability. An organic light emitting device including an organic layer formed of the triarylamine-based compound has high efficiency, low operating voltage, great luminance, and long lifetime.

15 Claims, 9 Drawing Sheets

U.S. PATENT DOCUMENTS

| | | | |
|---|---|---|---|
| 5,639,914 | A | 6/1997 | Tomiyama et al. |
| 6,465,115 | B2 | 10/2002 | Shi et al. |
| 6,646,164 | B2 | 11/2003 | Uemura et al. |
| 7,615,777 | B2 * | 11/2009 | Lee ................................ 257/40 |
| 2002/0128514 | A1 | 9/2002 | Uemura et al. |
| 2003/0143430 | A1 | 7/2003 | Kawamura et al. |

FOREIGN PATENT DOCUMENTS

| | | |
|---|---|---|
| EP | 0 506 492 A2 | 9/1992 |
| EP | 0 650 955 A1 | 5/1995 |
| EP | 1 029 909 | 8/2000 |
| EP | 1 148 109 A2 | 10/2001 |
| EP | 1 553 079 A2 | 7/2005 |
| JP | 07-301926 * | 11/1995 |
| JP | 2000-086595 | 3/2000 |
| JP | 2002-356462 | 12/2002 |
| JP | 2004-047442 * | 2/2004 |
| JP | 2004-182740 | 7/2004 |
| KR | P1995-0011398 | 5/1995 |

OTHER PUBLICATIONS

Korean Office Action for corresponding Korean Patent Application No. 2005-0066959, issued on Sep. 28, 2006.

"Improved Functional Group Compatibility in the Palladium-Catalyzed Synthesis of Aryl Amines" to Harris, et al. Organic Letters, vol. 4, No. 17 2885-2888 (2002).

"Improved Performance of Organic Light-emitting Diodes with a New Hole-transporting Material" to Kim, et al. Chemistry Letters, vol. 35, No. 1 (2006).

European Search Report for corresponding Korean Patent Application No. 2005-0066959, issued on Nov. 17, 2006.

"Dynamic Assembly of Coordination Boxes from (en) Pd (II) Unit and a Rectangular Panel-Likne Ligand" to Yamanoi, et al. NMR, CSI-MS, and X-ray studies,123, 980-981 (2001).

Chinese Office Action issued by Chinese Patent Office on Jun. 10, 2010 corresponding to Korean Patent Application No. 2005-0066959 and Request for Entry of the Accompanying Office Action attached herewith.

Request for Entry of the Accompanying Office Action for Japanese Office action attached herewith.

Office action from Japanese Patent Office issued in Applicant's corresponding Japanese Patent Application No. 2006-201239 dated Oct. 15, 2009.

Chem Abstract: 1996:56604; Kadoi et al, The Office Action (Paper No. 20080816) mailed on Aug. 19, 2008 of the related U.S. Appl. No. 11/489,565.

Abstract of JP application No. 1994-95327 to Kadoi et al., entitled *Electrophotographic Photoreceptor Containing Tetraminodiphenyl Derivative Charge Transporting Agent* which corresponds to Japanese published patent document No. JP 07-301926 (published Nov. 1995).

* cited by examiner

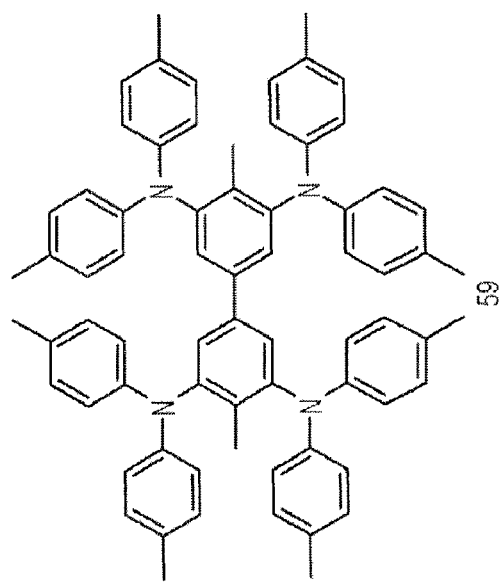
FIG. 5
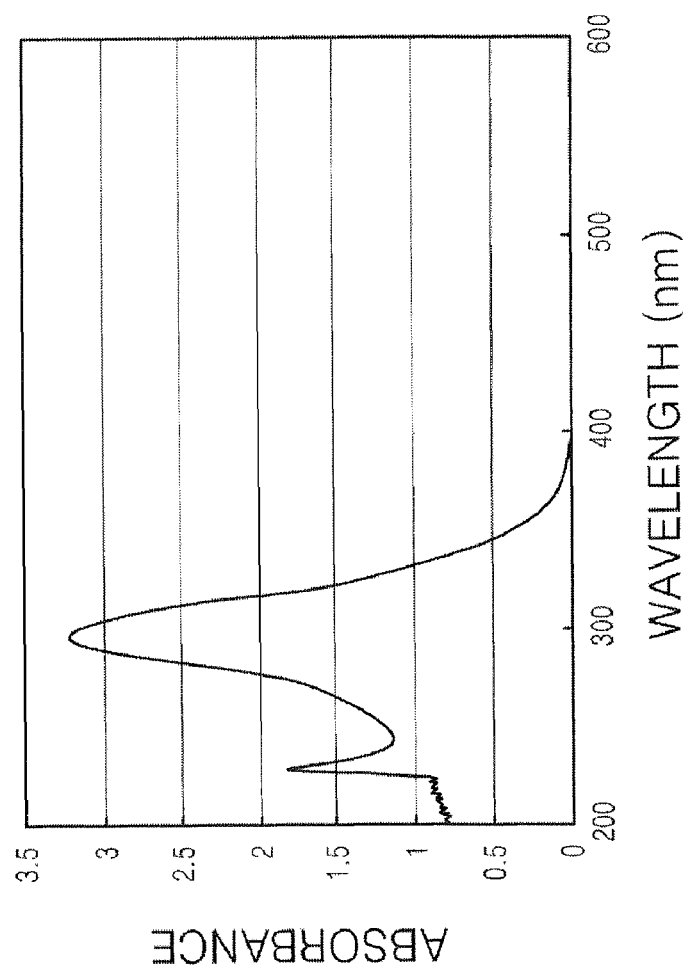

TRIARYLAMINE-BASED COMPOUND, METHOD OF PREPARING THE SAME, AND ORGANIC LIGHT EMITTING DEVICE USING THE TRIARYLAMINE-BASED COMPOUND

CROSS-REFERENCE TO RELATED PATENT APPLICATIONS AND CLAIM OF PRIORITY

This application claims the benefit of Korean Patent Application No. 10-2005-0066959, filed on Jul. 22, 2005, in the Korean Intellectual Property Office, the disclosure of which is incorporated herein in its entirety by reference. Furthermore, this application is a divisional of Applicants' Ser. No. 11/489,565 filed in the U.S. Patent & Trademark Office on 20 Jul. 2006 now abandoned, and assigned to the assignee of the present invention.

BACKGROUND OF THE INVENTION

1. Field of the Invention

The present invention relates to a triarylamine-based compound, to a method of preparing the same, and to an organic light emitting device using the triarylamine-based compound, and more particularly, to a triarylamine-based compound which is electrically stable, has a high charge transporting capability and a high glass transition temperature, and prevents crystallization, to a method of preparing the same, and to an organic light emitting device having high efficiency, high luminance, long lifetime, and a low turn-on voltage, which includes an organic layer containing the triarylamine-based compound.

2. Description of the Related Art

Organic light emitting devices, which are self-emissive display devices, are highlighted due to many advantages such as a wide viewing angle, high contrast, and a short response time.

In general, an organic light emitting device has a stacked structure of anode/emission layer/cathode. In some cases, a hole injection layer, a hole transport layer, an electron injection layer, and an electron transport layer may be further deposited between the anode and the emission layer or between the emission layer and the cathode, thereby forming stacked structures such as anode/hole injection layer/hole transport layer/emission layer/cathode, anode/hole injection layer/hole transport layer/emission layer/electron injection layer/cathode, and anode/hole injection layer/hole transport layer/emission layer/electron transport layer/electron injection layer/cathode.

It is known that a hole transport layer can be formed of a triphenylamine derivative or an anthracene derivative (U.S. Pat. Nos. 6,646,164 and 6,465,115.)

However, when a hole transport layer formed of such a material described above is used to produce an organic light emitting device, the obtained organic light emitting device has a short lifetime, low efficiency and high power consumption. Therefore, there is a need to develop a hole transport layer forming material to produce an efficient organic light emitting display having a long lifetime and a low turn-on voltage.

SUMMARY OF THE INVENTION

The present invention provides a material that is electrically stable, has a high electron transporting capability and a high glass transition temperature, and prevents crystallization. The material is capable of transporting or injecting holes as required for a fluorescent or phosphorescent device emitting all colors including red, green, blue, white, etc.

The present invention also provides a method of preparing the same.

The present invention also provides an organic light emitting device having high efficiency, high luminance, long lifetime, and a low turn-on voltage, which includes an organic layer containing the triarylamine-based compound.

According to an aspect of the present invention, there is provided a triarylamine-based compound of formula 1:

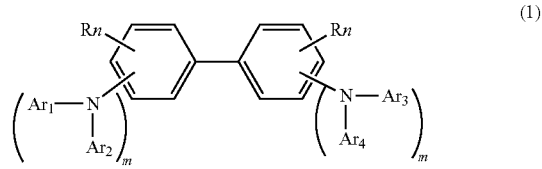

where $Ar_1$ through $Ar_4$ are independently a substituted or unsubstituted C6-C30 aryl group or a substituted or unsubstituted C2-C30 heterocyclic group;

each R is independently a halogen atom, a cyano group, a substituted or unsubstituted C1-C30 alkyl group;

n is an integer of 1 through 3; and m is an integer of 1 through 3.

According to another aspect of the present invention, there is provided a method of preparing a triarylamine-based compound of formula 1 by reacting compounds of formulae 8 through 10:

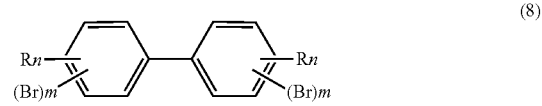

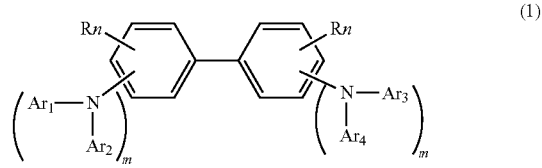

where $Ar_1$ through $Ar_4$ are independently a substituted or unsubstituted C6-C30 aryl group or a substituted or unsubstituted C2-C30 heterocyclic group;

each R is independently a halogen atom, a cyano group, a substituted or unsubstituted C1-C30 alkyl group;

n is an integer of 1 through 3; and m is an integer of 1 through 3.

According to still another aspect of the present invention, there is provided an organic light emitting device including an organic layer interposed between a first electrode and a second electrode, wherein the organic layer contains the triarylamine-based compound.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein:

FIG. 5 shows a UV spectrum and the structure of Compound 59 prepared according to an embodiment of the present invention;

DETAILED DESCRIPTION OF THE PREFERRED EMBODIMENTS

Figure 1A:
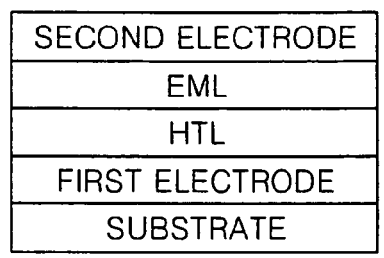
FIGS. 1A through 1C illustrate structures of an organic light emitting device according to embodiments of the present invention.

The present invention will be described in detail with reference to drawings.

The present invention provides an organic emission compound that may be electrically stable, has a high electron transporting capability and a high glass transition temperature, and prevents crystallization. The material may be capable of transporting or injecting holes as required for a fluorescent or phosphorescent device emitting all colors including red, green, blue, white, etc.

The compound of embodiments of the present invention have two or more, preferably, four or more triarylamine derivatives and two or more halogen atoms or alkyl groups as a side chain, a method of preparing the organic emission compound, and an organic light emitting device in which the organic emission compound is used to form an organic layer such as a hole injection layer, a hole transport layer, and an emission layer.

The compound according to an embodiment of the present invention may be a compound represented by Formula 1:

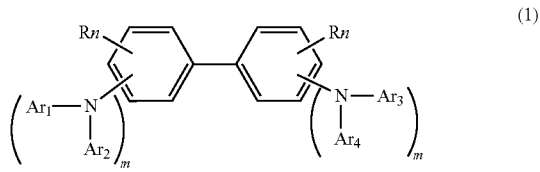

(1)

where $Ar_1$ through $Ar_4$ are independently a substituted or unsubstituted C6-C30 aryl group or a substituted or unsubstituted C2-C30 heterocyclic group;

each R is independently a halogen atom, a cyano group, a substituted or unsubstituted C1-C30 alkyl group;

n is an integer of 1 through 3; and m is an integer of 1 through 3.

In formula 1, each of $Ar_1$ through $Ar_4$ is a phenyl group, a methylphenyl group, a dimethyl group, a trimethyl group, an ethylphenyl group, an ethylbiphenyl, an o-, m- or p-fluorophenyl group, a dichlorophenyl group, a dicyanophenyl group, a trifluoromethoxyphenyl group, an o-, m- or p-tolyl group, an o-, m- or p-cumenyl group, a mesityl group, a phenoxyphenyl group, a ($\alpha,\alpha$-dimethylbenzene)phenyl group, a (N,N'-dimethyl)aminophenyl group, a (N,N'-diphenyl)aminophenyl group, a pentalenyl group, an indenyl group, a naphthyl group, a methylnaphthyl group, an anthracenyl group, an azurenyl group, a heptarenyl group, an acenaphthylrenyl group, a phenalenyl group, a fluorenyl group, an anthraquinolyl group, a methyl anthryl group, a phenanthrenyl group, a triphenylene group, a pyrenyl group, a chrysenyl group, an ethyl-chrysenyl group, a picenyl group, a perylenyl group, a chloroperylenyl group, a pentaphenyl group, pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a lower alkylcarbazolyl group, a biphenyl group, a lower alkyl phenyl group, a lower alkoxy phenyl group, a thiophenyl group, an indolyl group, or a pyridyl group. The lower alkyl group may be a C1-C5 alkyl group, and the lower alkoxy group may be a C1-C5 alkoxy group.

For example, each of $Ar_1$ through $Ar_4$ may be an aryl group substituted with one, two, or three substituents selected from a C1-C5 lower alkyl group, a C1-C5 lower alkoxy group, a cyano group, a phenoxy group, a phenyl group, or a halogen atom, wherein the aryl group is preferably a phenyl group, or a naphthyl group.

In Formula 1, R may be a C1-C10 alkyl group such as a methyl group, an ethyl group, or a butyl group.

Substituents contained in formulae described through the specification will now be defined.

The aryl group contained in formulae through the specification refers to a C6-C30 carbocyclic aromatic system including one or more rings, which are pendent to each other or fused together. The aryl group may be a phenyl group, a naphthyl group, or a tetrahydronaphthyl group. The aryl group may have a substituent selected from a halogen atom, a nitro group, a cyano group, a hydroxy group, a C1-C10 alkoxy group, and a C1-C10 alkyl group.

The heterocyclic group contained in formulae through the specification refers to a heteroaryl group or a carbocyclic system containing a heteroatom, wherein at least one hydrogen atom of the heterocyclic group can be substituted with the substituents described above when the aryl group is defined.

The heteroaryl group contained in formulae through the specification refers to an aromatic group which contains one, two, or three heteroatoms selected from N, O, P and S and the unselected cyclic atom is C. The heteroaryl group may be a pyridyl group, or the like.

The carbocyclic group containing a heteroatom refers to a cycloalkyl group containing one, two, or three heteroatoms selected from N, O, P and S. Such a cycloalkyl group may be a tetrahydrofuranyl group.

Examples of the C1-C30 alkyl group may be methyl, ethyl, propyl, isobutyl, pentyl, iso-amyl, hexyl, or the like, wherein at least one hydrogen atom of the alkyl group may be a substituent selected from a halogen atom, a nitro group, a cyano group, a hydroxy group, a C1-C10 alkoxy group, and a C1-C10 alkyl group.

The other groups, which are not described above, are construed in such a way as conventionally regarded by a person having ordinary skill in the art.

The triarylamine-based compound of formula 1 according to an embodiment of the present invention has a high steric effect due to two or more, preferably, four or more triarylamine derivatives, having two or more halogen atoms or alkyl groups. As a result, the triarylamine-based compound of formula 1 has a high glass transition temperature or a high melting point. In other word, the triarylamine-based compound of formula 1 has high resistance to heat generated within an organic layer, at the interface between organic layers, or at the interface between an organic layer and a metallic electrode when the triarylamine-based compound of formula 1 emits light, and withstands under high temperature conditions. Accordingly, an organic light emitting device including a hole injection layer, a hole transport layer, or an emission layer formed of the triarylamine-based compound of formula 1 as a host exhibits great luminance and is suitable for emission over a long period of time. In addition, since the biphenyl ring is substituted with two or more, for example, four or more bulky triarylamines and two or more alkyl group or halogen atoms, crystallization is prevented owing to steric effects.

Since the organic light emitting device according to an embodiment of the present invention includes an organic layer containing two or more triarylamine derivatives to have a high glass transition temperature, the organic light emitting device has high durability when operates or is deposited in a shelf.

The triarylamine-based compound of formula 1 may be one of compounds of formulae 2 through 4:

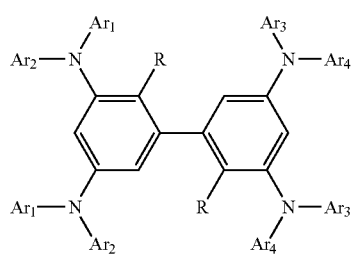

(2)

where $Ar_1$ through $Ar_4$ are as described above and R is a C1-C10 alkyl group;

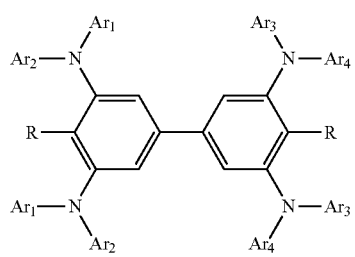

(3)

where $Ar_1$ through $Ar_4$ are as described above and R is a C1-C10 alkyl group; and

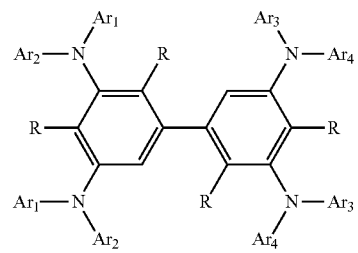

(4)

where $Ar_1$ through $Ar_4$ are as described above and R is a C1-C10 alkyl group.

In formulae 2 through 4, each of $Ar_1$ through $Ar_4$ is a phenyl group, an o-tolyl group, a m-tolyl group, a p-tolyl group, a 3,5-dimethylphenyl group, a 4-chlorophenyl group, a 3-chlorophenyl group, a 2-chlorophenyl group, a 4-methoxy phenyl group, a 3-methoxyphenyl group, a 2-methoxyphenyl group, a 4-butylphenyl group, a 4-ethylphenyl group, a 3-ethylphenyl group, a 2-ethylphenyl group, a 3,5-diethylphenyl group, a 4-isopropylphenyl group, a 3-isopropylphenyl group, a 2-isopropylphenyl group, a 3,5-diisopropylphenyl group, a 4-bromophenyl group, a 3-bromophenyl group, a 2-bromophenyl group, a 4-octyphenyl group, a 3-octyphenyl group, a 2-octyphenyl group, a 2,4-dioctyl phenyl group, a 2,6-dimethylphenyl group, a 2,4,4-trimethylphenyl group, a 2,6-dimethylphenyl group, a 2,4,6-trimethylphenyl group, a 1-naphthyl group, a 2-naphthyl group, a 1-anthracenyl group, or a 2-anthracenyl group; and R is a methyl group.

In formulae 2 through 4, $Ar_1$ and $Ar_2$ are the same and $Ar_1$ and $Ar_2$ are a phenyl group, a 4-butylphenyl group, a p-tolyl group, a m-tolyl group, an o-tolyl group, a 3,5-dimethylphenyl group, a 4-cyanophenyl group, a 4-methoxyphenyl group, a 2,4-dimethylphenyl group, or a 2,4,6-trimethylphenyl group; each of $Ar_3$ and $Ar_4$ is a phenyl group, a 4-methoxyphenyl group, a p-tolyl group, a m-tolyl group, an o-tolyl group, a 1-naphthyl group, a 2-naphthyl group, a 1-anthracenyl group, or a 2-anthracenyl group; and R is a methyl group.

Examples of the triarylamine-based compounds represented by formula 2 through 4 will now be described. However, the triarylamine-based compounds represented by formulae 1 through 4 are not limited thereto.

The triarylamine-based compound represented by formula 2 may be one of the compounds of Formula 5 with the $Ar_1$ through $Ar_4$ groups as shown in the below table:

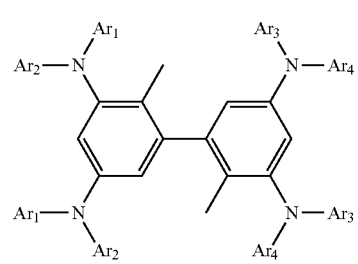

(5)

where $Ar=Ar_1=Ar_2=Ar_3=Ar_4$

Where $Ar_1$ through $Ar_4$ are the same, particular examples of $Ar_1$ through $Ar_4$ of the triarylamine-based compound represented by Formula 5 include the followings, but are not limited thereto.

| No. | Ar |
|---|---|
| 1 | phenyl |
| 2 | 4-methylphenyl |
| 3 | 3-methylphenyl |
| 4 | 2-methylphenyl |
| 5 | 3,5-dimethylphenyl |
| 6 | 4-chlorophenyl |
| 7 | 3-chlorophenyl |
| 8 | 2-chlorophenyl |
| 9 | 4-methoxyphenyl |
| 10 | 3-methoxyphenyl |
| 11 | 2-methoxyphenyl |
| 12 | 4-C$_4$H$_9$-phenyl |

-continued

| No. | Ar |
|---|---|
| 13 | 4-C$_2$H$_5$-phenyl |
| 14 | 3-C$_2$H$_5$-phenyl |
| 12 | 2-C$_2$H$_5$-phenyl |
| 13 | 3,5-di-C$_2$H$_5$-phenyl |
| 14 | 4-isoC$_3$H$_7$-phenyl |
| 15 | 3-isoC$_3$H$_7$-phenyl |
| 16 | 2-isoC$_3$H$_7$-phenyl |
| 17 | 3,5-di-isoC$_3$H$_7$-phenyl |
| 18 | 4-bromophenyl |
| 19 | 3-bromophenyl |
| 20 | 2-bromophenyl |

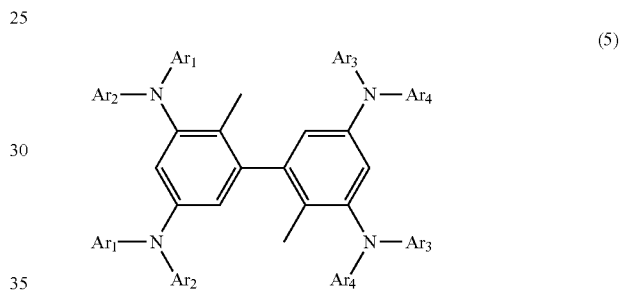
Ar=Ar$_1$=Ar$_2$, and Ar'=Ar$_3$=Ar$_4$
Where Ar$_1$ and Ar$_2$ are the same and Ar$_3$ and Ar$_4$ are the same, particular examples of Ar$_1$ through Ar$_4$ of the triarylamine-based compound represented by Formula 5 include the followings, but are not limited thereto.

| No. | Ar | Ar' |
|---|---|---|
| 38 | 3,5-dimethylphenyl | phenyl |
| 39 | 4-cyanophenyl | phenyl |
| 40 | 4-methoxyphenyl | phenyl |
| 41 | 4-methylphenyl | 4-methoxyphenyl |
| 42 | 3,4-dimethylphenyl | 4-methoxyphenyl |
| 43 | 2,3-dimethylphenyl | 4-methoxyphenyl |
| 44 | 2,4-dimethylphenyl | phenyl |
| 45 | 2,4-dimethylphenyl | 4-methylphenyl |
| 46 | 2,4-dimethylphenyl | 2-methylphenyl |
| 47 | 3,4,5-triethylphenyl | 4-methylphenyl |
| 48 | 3,4,5-triethylphenyl | 2-methylphenyl |
| 49 | phenyl | 1-naphthyl |
| 50 | phenyl | 2-naphthyl |
| 51 | phenyl | 1-anthracenyl |
| 52 | phenyl | 2-anthracenyl |
| 53 | 4-methylphenyl | 2-naphthyl |
| 54 | 4-methylphenyl | 2-anthracenyl |
| 55 | 4-methoxyphenyl | 2-naphthyl |
| 56 | 4-methoxyphenyl | 2-anthracenyl |
| 57 | 3,4-dimethylphenyl | 2-naphthyl |

The triarylamine-based compound represented by formula 3 may be one of the compounds of Formula 6 with the $Ar_1$ through $Ar_4$ groups as shown in the below table:

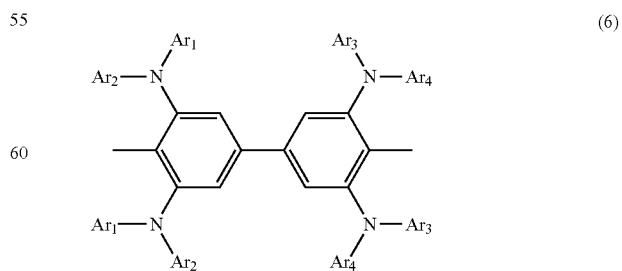

(6)

$Ar = Ar_1 = Ar_2 = Ar_3 = Ar_4$

Where $Ar_1$ through $Ar_4$ are the same, particular examples of $Ar_1$ through $Ar_4$ of the triarylamine-based compound represented by Formula 6 include the followings, but are not limited thereto.
| No. | Ar |
|---|---|
| 58 | 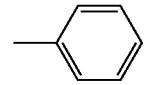 |
| 59 | 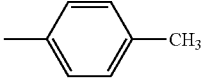 |
| 60 | 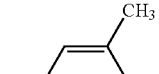 |
| 61 | 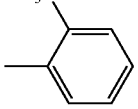 |
| 62 | 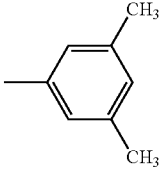 |
| 63 |  |
| 64 | 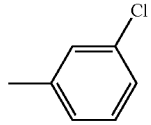 |
| 65 | 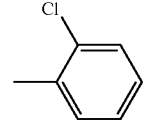 |
| 66 | 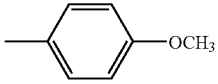 |
| 67 | 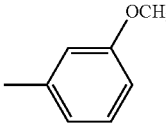 |
| 68 | 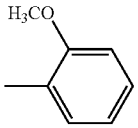 |
| 69 | 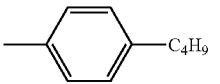 |
| 70 | 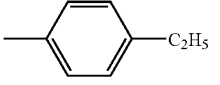 |
| 71 | 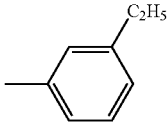 |
| 72 | 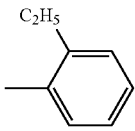 |
| 73 | 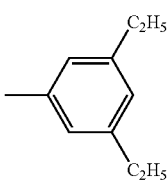 |
| 74 | 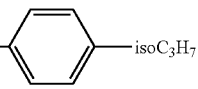 |
| 75 | 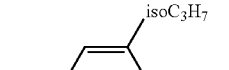 |
| 76 | 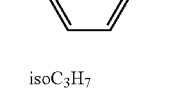 |
| 77 | 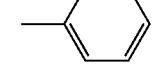 |
| 78 | 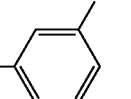 |
| 79 | 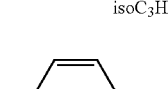 |

| No. | Ar |
|---|---|
| 80 | 1-bromo-2-methylbenzene |
| 81 | 4-octyl-methylbenzene |
| 82 | 3-octyl-methylbenzene |
| 82 | 2-octyl-methylbenzene |
| 84 | 2,4-dimethyl (H₃C groups) |
| 85 | 2,3,4-trimethyl |
| 86 | 2,3,5-trimethyl |
| 87 | 2,5-diethyl |
| 88 | 2,3,6-triethyl-type |
| 89 | 2,3,5-triethyl |

| No. | Ar |
|---|---|
| 90 | 1-naphthyl |
| 91 | 2-naphthyl |
| 92 | 1-anthracenyl-methyl |
| 93 | 2-anthracenyl |

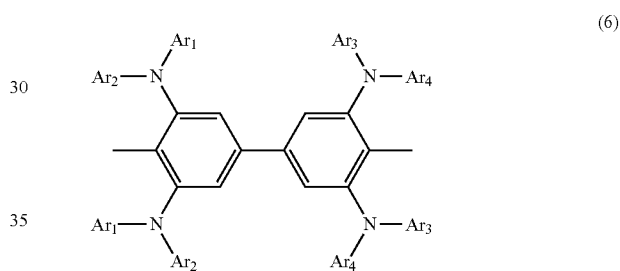

(6)

Ar=Ar₁=Ar₂, and Ar'=Ar₃=Ar₄

Where $Ar_1$ and $Ar_2$ are the same and $Ar_3$ and $Ar_4$ are the same, particular examples of $Ar_1$ through $Ar_4$ of the triarylamine-based compound represented by Formula 6 include the followings, but are not limited thereto.

| No. | Ar | Ar' |
|---|---|---|
| 94 | 4-butylphenyl | phenyl |
| 95 | 4-methylphenyl | phenyl |
| 96 | 3-methylphenyl | phenyl |
| 97 | 2-methylphenyl | phenyl |

| No. | Ar | Ar' |
|---|---|---|
| 98 | | |
| 99 | | |
| 100 | | |
| 101 | | |
| 102 | | |
| 103 | | |
| 104 | | |
| 105 | | |
| 106 | | |
| 107 | | |
| 108 | | |
| 109 | | |
| 110 | | |
| 111 | | |
| 112 | | |
| 113 | | |
| 114 | | |
| 115 | | |
| 116 | | |
| 117 | | |
The triarylamine-based compound represented by formula 4 may be one of the compounds of Formula 7 with the $Ar_1$ through $Ar_4$ groups as shown in the below table:
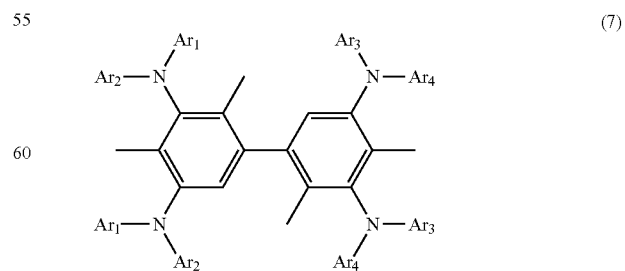
(7)
$Ar=Ar_1=Ar_2=Ar_3=Ar_4$ Where Ar$_1$ through Ar$_4$ are the same, particular examples of Ar$_1$ through Ar$_4$ of the triarylamine-based compound represented by Formula 7 include the followings, but are not limited thereto.
| No. | Ar |
|---|---|
| 118 | 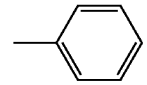 |
| 119 | 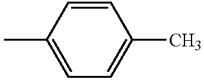 |
| 120 | 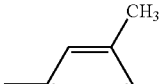 |
| 121 | 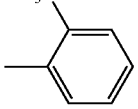 |
| 122 | 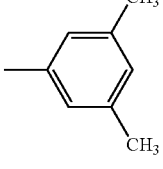 |
| 123 |  |
| 124 | 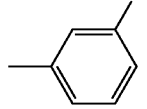 |
| 125 | 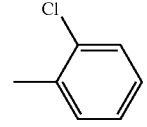 |
| 126 | 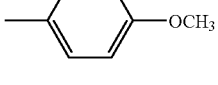 |
| 127 | 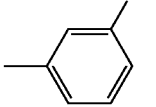 |
| 128 | 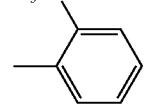 |
-continued
| No. | Ar |
|---|---|
| 129 | 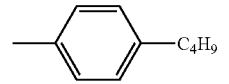 |
| 130 | 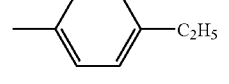 |
| 131 | 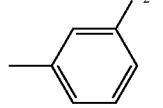 |
| 132 | 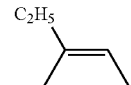 |
| 133 | 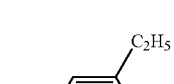 |
| 134 | 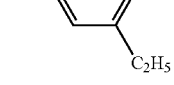 |
| 135 | 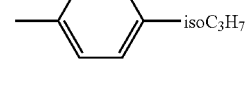 |
| 136 | 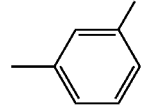 |
| 137 | 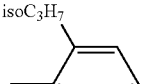 |
| 138 | 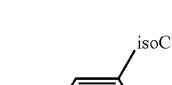 |
| 140 | 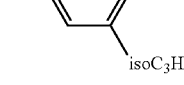 |

| No. | Ar |
|---|---|
| 141 | 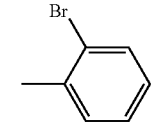 |
| 142 |  |
| 143 | 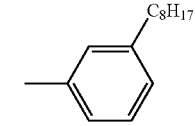 |
| 144 | 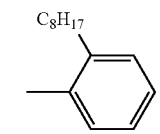 |
| 145 | 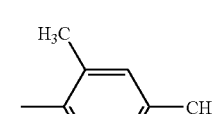 |
| 146 | 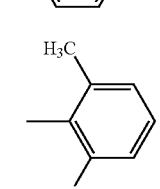 |
| 147 | 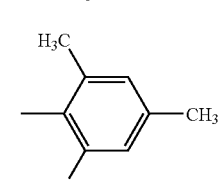 |
| 148 | 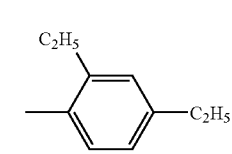 |
| 149 | 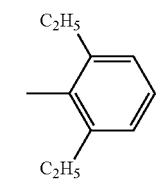 |
| 150 | 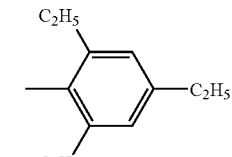 |
| No. | Ar |
|---|---|
| 151 | 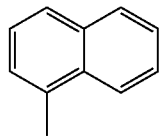 |
| 152 | 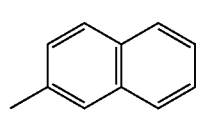 |
| 153 | 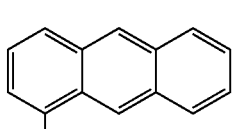 |
| 154 | 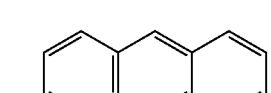 |
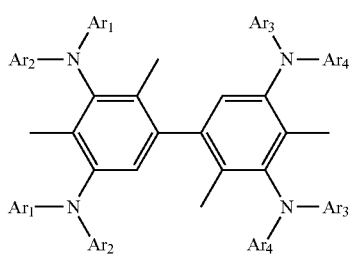 (7)
$Ar=Ar_1=Ar_2$, and $Ar'=Ar_3=Ar_4$
Where $Ar_1$ and $Ar_2$ are the same and $Ar_3$ and $Ar_4$ are the same, particular examples of $Ar_1$ through $Ar_4$ of the triarylamine-based compound represented by Formula 7 include the followings, but are not limited thereto.
| No. | Ar | Ar' |
|---|---|---|
| 155 | 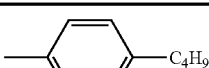 | 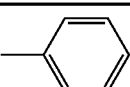 |
| 156 |  | 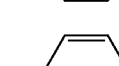 |
| 157 | 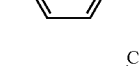 | 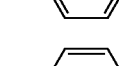 |

-continued

| No. | Ar | Ar' |
|---|---|---|
| 158 | 2,3-dimethylphenyl | phenyl |
| 159 | 3,5-dimethylphenyl | phenyl |
| 160 | 4-cyanophenyl | phenyl |
| 161 | 4-methoxyphenyl | phenyl |
| 162 | 4-methylphenyl | 4-methoxyphenyl |
| 163 | 3-methylphenyl | 4-methoxyphenyl |
| 164 | 2,3-dimethylphenyl | 4-methoxyphenyl |
| 165 | 2,5-dimethylphenyl | phenyl |
| 166 | 2,4-dimethylphenyl | 4-methylphenyl |
| 167 | 2,4-dimethylphenyl | 2-methylphenyl |
| 168 | 3,4,5-triethylphenyl | 4-methylphenyl |

-continued

| No. | Ar | Ar' |
|---|---|---|
| 169 | 3,4,5-triethylphenyl | 2-methylphenyl |
| 170 | phenyl | 1-naphthyl |
| 171 | phenyl | 2-naphthyl |
| 172 | phenyl | 1-anthryl |
| 173 | phenyl | 2-anthryl |
| 174 | 4-methylphenyl | 2-naphthyl |
| 175 | 4-methylphenyl | 2-anthryl |
| 176 | 4-methoxyphenyl | 2-naphthyl |
| 177 | 4-methoxyphenyl | 2-anthryl |
| 178 | 2,4-dimethylphenyl | 2-naphthyl |

An exemplary method of preparing a triarylamine-based compound of formula 1 will now be described.

First, a triarylamine-based compound of formula 1 is prepared by reacting compounds of formulae 8 through 10:

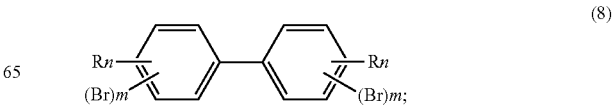

(8)

-continued

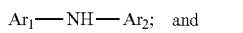  (9)

  (10)

where each of $Ar_1$ through $Ar_4$ is a substituted or unsubstituted C6-C30 aryl group or a substituted or unsubstituted C2-C30 heterocyclic group, each R is independently a halogen atom, a cyano group, a substituted or unsubstituted C1-C30 alkyl group, n is an integer of 1 through 3, and m is an integer of 1 through 3.

The reaction of the compounds represented by formulae 8 through 10 are performed in the presence of tri(dibenzylideneacetone)dipalladium(0) ($Pd_2(dba)_3$ where dba is an abbreviation of dibenzylideneacetone) at a reaction temperature of 50 to 150° C.

In order to obtain the compound of formula 8, a compound of formula 11 is reacted with butyl lithium and then the reactant product is reacted with copper chloride. Such a coupling reaction may be performed at a reaction temperature of 0 through −78° C.

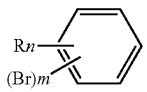  (11)

where each R is independently a halogen atom, a cyano group, or a substituted or unsubstituted C1-C30 alkyl group; n is an integer of 1 to 3, m is an integer of 1 through 3.

In an organic light emitting device according to an embodiment of the present invention, an organic layer containing the triarylamine-based compound of formula 1 can be a hole injection layer, a hole transport layer, or a single layer having hole injecting and hole transporting capabilities.

The organic light emitting device may have a stacked structure of first electrode/hole transport layer/emission layer/second electrode, first electrode/hole injection layer/hole transport layer/emission layer/electron transport layer/second electrode, or first electrode/hole injection layer/hole transport layer/emission layer/electron transport layer/electron injection layer/second electrode.

The emission layer may be formed of a phosphorescent material or a fluorescent material.

In the organic light emitting device according to an embodiment of the present invention, the triarylamine-based compound of formula 1 can be used as an emission layer forming fluorescent or phosphorescent host.

A method of producing an organic light emitting device will now be described in detail.

Figure 1B:
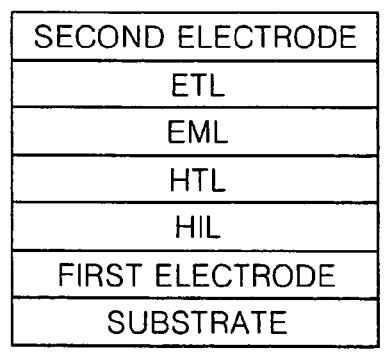
Figure 1C:
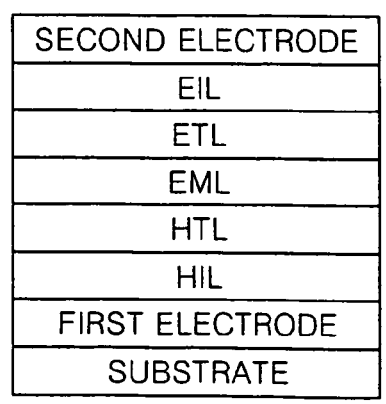

FIGS. 1A through 1C illustrate sectional views of organic light emitting devices according to embodiments of the present invention.

Referring to FIG. 1A, an organic light emitting device according to an embodiment of the present invention includes a first electrode, a hole transport layer (HTL) and an emission layer (EML) sequentially deposited on the first electrode, and a second electrode formed on the emission layer.

Referring to FIG. 1B, an organic light emitting device according to another embodiment of the present invention has the same stacked structure as the organic light emitting device illustrated in FIG. 1A, except that a hole injection layer (HIL) is further formed between the first electrode and the hole transport layer (HTL) and an electron transport layer (ETL) is further formed between the emission layer (EML) and the second electrode.

Referring to FIG. 1C, an organic light emitting device according to still another embodiment of the present invention has the same stacked structure as the organic light emitting device illustrated in FIG. 1B, except that an electron injection layer (ETL) is further formed between the electron transport layer (ETL) and the second electrode.

An exemplary method of preparing organic light emitting devices having stacked structures described above will now be described.

First, a high work function anode material is deposited on a substrate using a depositing method or a sputtering method to form an anode, which can be a first electrode. The substrate may be a substrate that is commonly used in a conventional organic light emitting device. For example, the substrate may be formed of glass or transparent plastic, both of which have good mechanical strength, thermal stability, surface smoothness, transparency and waterproof, and can be easily handled. The anode material may be a conductive transparent material such as indium tin oxide (ITO), indium zinc oxide (IZO), tin oxide ($SnO_2$), zinc oxide (ZnO), and the like.

A hole injection layer is optionally formed on the anode.

More particularly, a hole injecting material is deposited using a vacuum depositing method, a spin coating method, a casting method, a LB method, or the like to form the hole injection layer. For example, the hole injection layer may be formed by vacuum deposition, which is suitable for obtaining a uniform film and preventing occurrence of pinholes.

When the hole injection layer is formed by vacuum deposition, deposition conditions may vary according to substances for hole injection layer and the structure and thermal properties of a hole injection layer which will be formed. For example, a deposition temperature may be in the range of 50 to 500° C., a degree of vacuum may be in the range of $10^{-8}$ to $10^{-3}$ torr, a deposition rate may be in the range of 0.01 to 100 Å/sec, and a thickness of the hole injection layer may be in the range of 10 Å to 5 μm.

The hole injection layer forming material is not be limited, and may be the triarylamine-based compound of formula 1 or selected from known hole injection layer forming materials. For example, the hole injection layer forming material may be a phthalocyanine compound such as copper phthalocyanine disclosed in U.S. Pat. No. 4,356,429 which is incorporated herein by reference; or a starburst type amine derivative such as 4,4',4"-tris(N-carbazolyl)triphenylamine (TCTA), 4,4',4"-tris(3-methylphenylphenylamino)triphenylamine (m-MTDATA), and 1,3,5-tris[4-(3-methylphenylphenylamino)phenyl]benzene (m-MTDAPB), disclosed in Advanced Material, 6, p. 677 (1994) which is incorporated herein by reference.

Then, a hole transport layer material is deposited on the hole injection layer by vacuum deposition, spin coating, casting, or LB. For example, the hole transport layer material may be deposited by vacuum deposition, which is suitable for obtaining a uniform layer and preventing occurrence of pinholes. When a hole transport layer is formed by vacuum deposition, deposition conditions may vary according to substances for forming hole transport layer, and, in general, may be the same as the hole injection layer.

The hole transport layer material is not limited, and may be the triarylamine-based compound of formula 1 according to an embodiment of the present invention or selected from known hole transport layer materials. For example, the hole transport layer material may be a carbazole derivative such as N-phenylcarbazole, polyvinylcarbazole, or the like; or a conventional amine derivative having an aromatic condensated ring such as N,N'-bis(3-methylphenyl)-N,N'-diphenyl-[1,1-biphenyl]-4,4'-diamine (TPD), N,N'-di(naphthalene-1-yl)-N,N'-diphenyl benzidine (α-NPD), or the like.

Subsequently, an emission layer material may be deposited on the hole transport layer by vacuum deposition, spin coating, casting, or LB. For example, the emission layer material may be deposited by vacuum deposition, which is suitable for obtaining a uniform layer and preventing occurrence of pinholes. When an emission layer is formed by vacuum deposition, deposition conditions may vary according to substances for forming an emission layer, and, in general, may be the same as the hole injection layer.

The emission layer material is not limited and may be the triarylamine-based compound of formula 1 as the fluorescent or phosphorescent host. In addition, $Alq_3$ can be used as a fluorescent host. A fluorescent dopant may be IDE102 or IDE105 commercially available from Idemitsu Inc., or C545T commercially available from Hayashibara Inc. A phosphorescent dopant may be a green phosphorescent dopant of $Ir(PPy)_3$ (PPy=2-phenylpyridine), a blue phosphorescent dopant of F2Irpic or a red phosphorescent dopant of RD 61 commercially available from UDC (Universal Display Corporation).

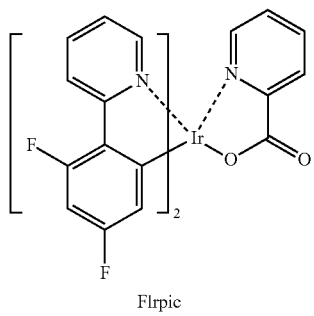

FIrpic

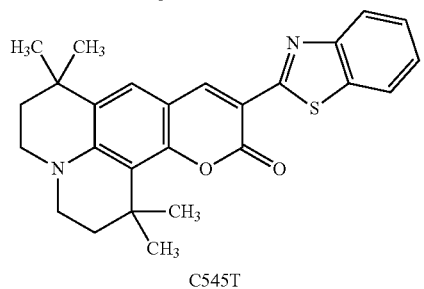

C545T

The concentration of the dopant may not be limited, and may be in the range of 0.01 to 15 parts by weight based on 100 parts by total weight of the host and the dopant.

When the emission layer contains a phosphorescent dopant, a hole blocking layer material may be deposited on the emission layer to form a hole blocking layer by vacuum deposition or spin coating, thereby blocking holes from being dispersing into an electron transport layer. The hole blocking layer material is not limited, and may be selected from known hole blocking layer materials such as an oxadiazole derivative, a triazole derivative, a phenanthroline derivative, or a hole blocking material disclosed in JP 11-329734(A1), which is incorporate herein by reference. For example, the hole blocking layer material can be aluminum(III)bis(2-methyl-8-quinolinato)4-phenylphenolate (BAlq) or 2,9-dimethyl-4,7-diphenyl-1,10-phenanthroline (BCP).

Then, an electron transport layer material may be deposited by vacuum deposition, spin coating, or casting to form an electron transport layer. For example, the electron transport layer material may be formed by vacuum deposition. The electron transport layer material can stably transport electrons injected from a cathode. The electron transport layer material is not limited, and may be a quinoline derivative such as tris(8-quinolinolate)aluminum ($Alq_3$). Furthermore, an electron injection layer can be formed on the electron transport layer to allow easy injection of electrons from the cathode.

The electron injection layer may be formed of LiF, NaCl, CsF, $Li_2O$, BaO, or the like. Although vacuum conditions for forming the hole blocking layer, the electron transport layer, the electron injection layer may vary according compounds, the hole injection layer is formed under the same vacuum conditions.

Subsequently, a cathode metal is deposited on the electron injection layer by, for example, vacuum deposition or sputtering, thereby forming a cathode, which is a second electrode. The cathode metal may be a low work function metal, alloy, or electrically conductive compound, or a mixture of these. Examples of the cathode may include Li, Mg, Al, Al—Li, Ca, Mg—In, Mg—Ag, and the like. Meanwhile, in order to obtain a front emission type display device, the cathode may be formed of ITO or IZO that is transparent.

The present invention will be described in further detail with reference to the following examples. These examples are for illustrative purposes only and are not intended to limit the scope of the present invention.

Synthesis Example 1

Preparing of Compound 2

Compound 2 was prepared through Reaction Scheme 1 below.

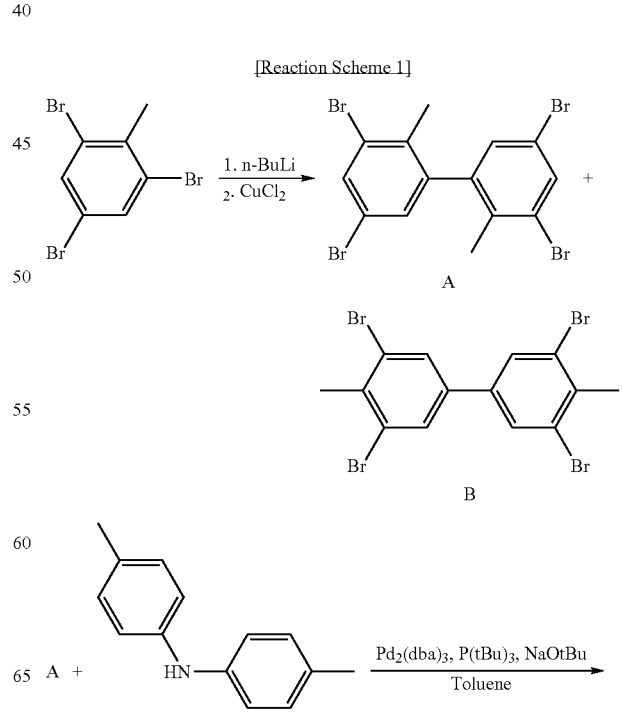

[Reaction Scheme 1]

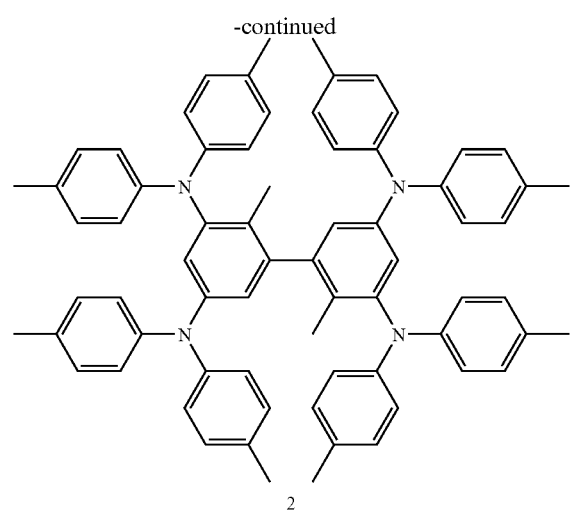

2

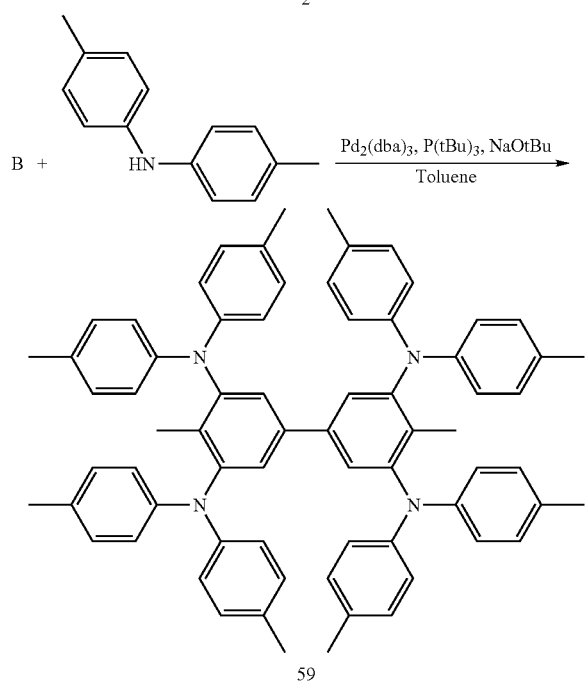

59

(Compound 2 and Compound 59 are the compound according to the No. 2 example and the compound according to the No. 59 example, respectively, in the above Tables.)

Synthesizing of Intermediates A and B 3.3 g (10 mmol) of 2,4,6-tribromotoluene was dissolved in 30 mL of diethylether. The resulting solution was cooled to −78° C. and 4.4 mL (11 mmol) of normalbutylithium (2.5 M in Hexane) was slowly added thereto. The resulting solution was stirred at −78° C. for one hour and 1.48 g (11 mmol) of copper chloride (II) was added thereto at −78° C.

The reactant product was stirred for 5 hours and cleaned using distilled water and ethylacetate at room temperature. The cleaned ethylacetate layer was dried over $MgSO_4$ and dried under a reduced pressure, thereby producing a crude-product. The pre-product was refined through a column chromatography and the refined result was recrystallized in dichloromethane and hexane, thereby producing white solid intermediates A and B. Amounts of A and B were 622 mg (yield 25%) and 746 mg (yield: 30%), respectively.

Intermediate A: $^1$H NMR ($CDCl_3$, 400 MHz) δ (ppm) 7.74 (d, 4H), 7.18 (d, 4H), 2.06 (s, 6H); $^{13}$C NMR ($CDCl_3$, 100 MHz) δ (ppm) 142.8, 134.9, 134.5, 131.1, 126.4, 119.4, 19.9

Intermediate B: $^1$H NMR ($CDCl_3$, 400 MHz) δ (ppm) 7.60 (s, 4H), 2.61 (s, 6H); $^{13}$C NMR ($CDCl_3$, 100 MHz) δ (ppm) 138.3, 137.2, 129.9, 125.8, 23.5

Synthesizing of Compound 2

380 mg (0.76 mmol) of the intermediate A, 903 mg (4.6 mmol) of di-para-tolylamine, 900 mg (9.4 mmol) of t-BuONa, 56 mg (0.06 mmol) of $Pd_2(dba)_3$, and 13 mg (0.06 mmol) of $P(t\text{-Bu})_3$ were dissolved in 5 mL of toluene, and the resulting solution was stirred at 90° C. for 3 hours.

The reactant product was cooled to room temperature and thrice extracted with distilled water and ethylacetate. The resulting organic layer was dried over $MgSO_4$ to evaporate the solvent. The remains were refined through a silica gel column chromatography to produce 670 mg of a white solid compound 2 (Yield: 91%.)

$^1$H NMR ($CD_2Cl_2$, 300 MHz) δ (ppm) 6.95-6.80 (m, 24H), 6.76 (d, 8H), 6.64 (s, 4H), 2.26 (s, 24H), 2.24 (s, 6H); $^{13}$C NMR ($CD_2Cl_2$, 100 MHz) δ (ppm) 147.4, 147.2, 146.1, 146.0, 145.0, 132.6, 131.1, 130.0, 130.3, 128.6, 124.8, 123.8, 122.3, 121.0, 21.6, 21.5, 15.8

Figure 2:
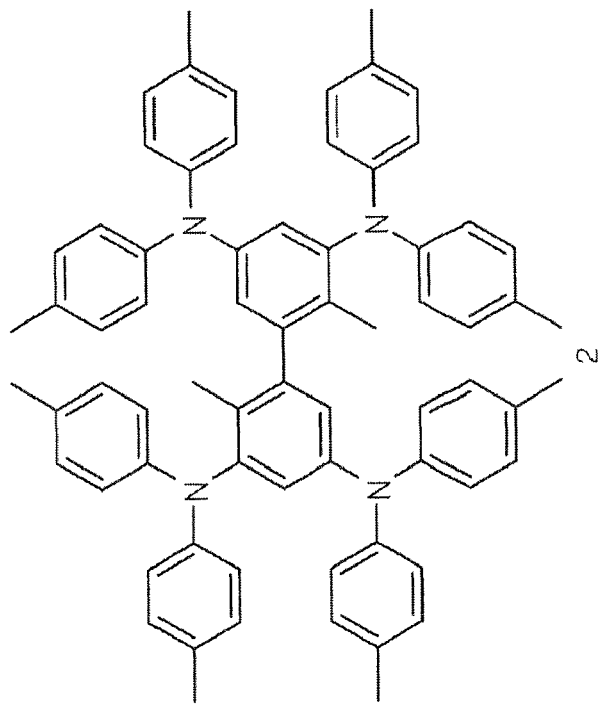
FIG. 2 shows a UV spectrum and the structure of Compound 2 prepared according to an embodiment of the present invention.
Figure 2:
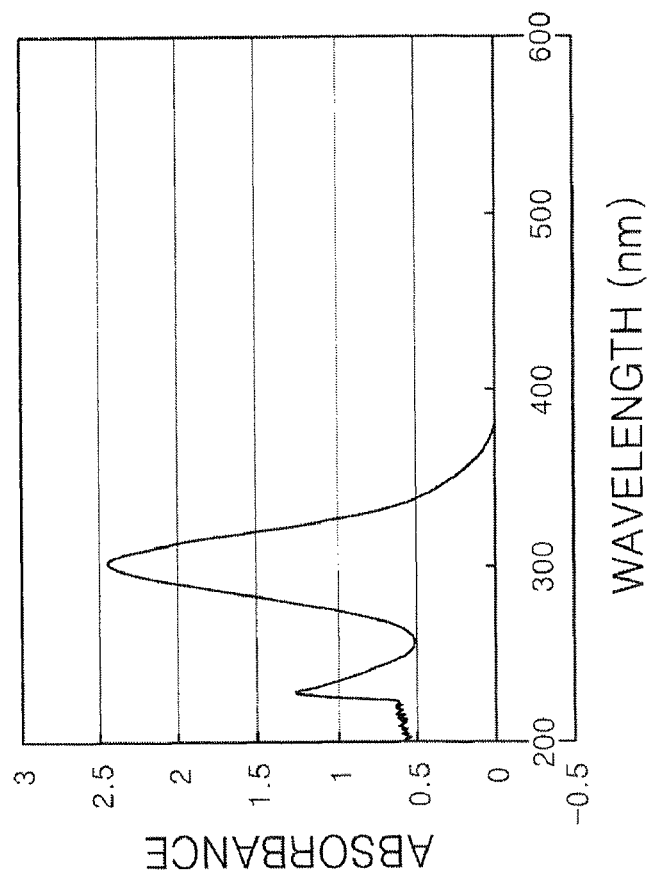

The compound 2 produced through the above mentioned process was diluted in $CHCl_3$ to 0.2 mM, and UV spectrum of the diluted solution was obtained. In the UV spectrum, the maximum absorption peaks appeared at 228 nm and 302 nm (FIG. 2).

Figure 3:
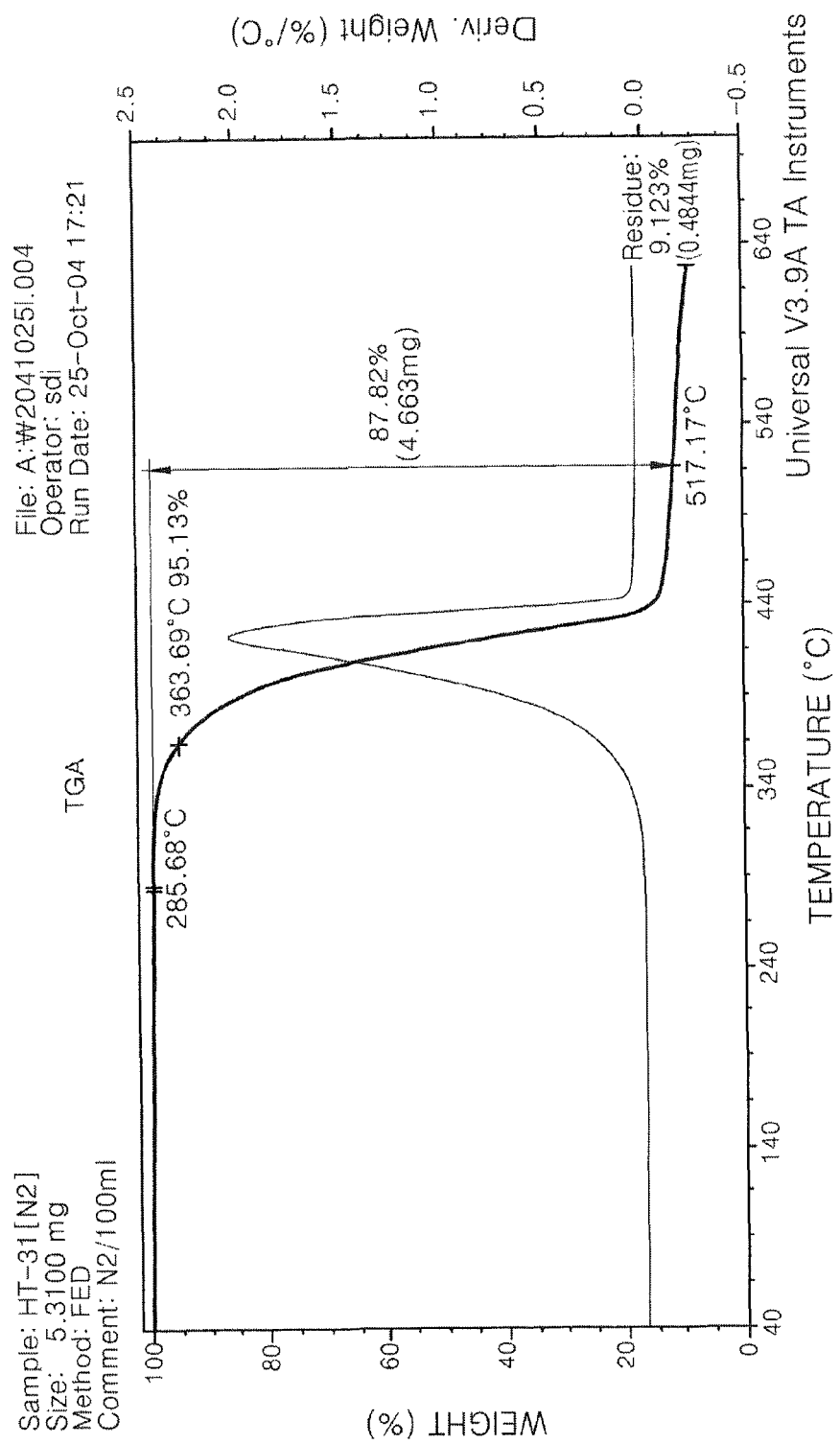
FIGS. 3 and 4 show results of thermogravimetric analysis (TGA) and differential scanning calorimetry (DSC) of Compound 2 prepared according to an embodiment of the present invention.
Figure 4:
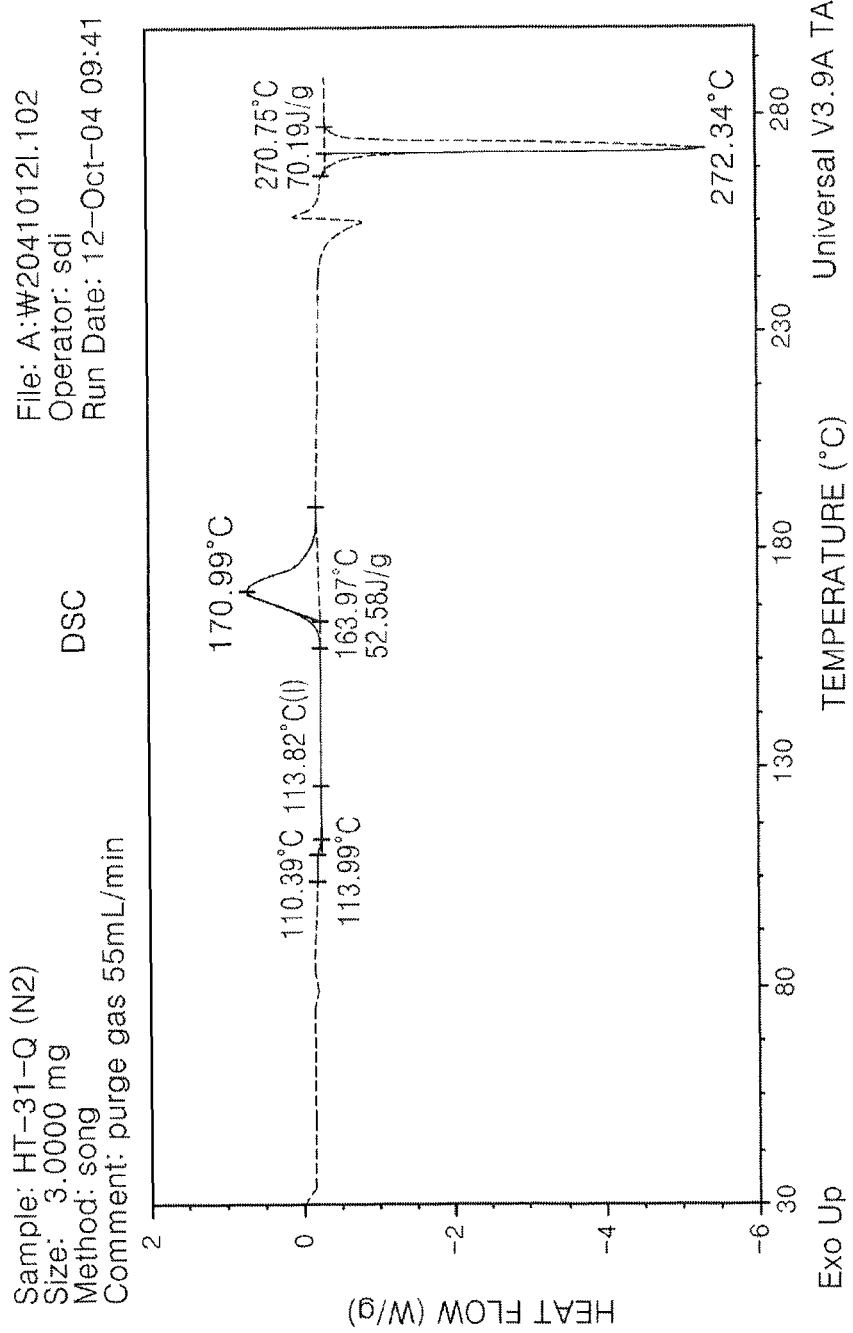

In addition, the compound 2 was thermally measured through thermo gravimetric analysis (TGA) and differential scanning calorimetry (DSC). TGA was performed using a Pt pan in disposable Al pan in a $N_2$ atmosphere while a temperature was increased by 10° C. per minute in a temperature range of room temperature to 600° C. DSC was performed using disposable Al pan in a $N_2$ atmosphere in a temperature range of room temperature to 400° C. As a result of such thermal analysis, Td was 364° C., Tg was 114° C., Tc was 171° C., and Tm was 272° C. (FIGS. 3 and 4.)

Highest occupied molecular orbital (HOMO) energy band and lowest occupied molecular orbital (LUMO) of the compound 2 were measured using an UV absorption spectrum and AC-2 that is an ionization potential measuring device. As a result, the HOMO and LUMO energy bands of the compound 2 were 5.35 eV and 2.11 eV, respectively.

Synthesis Example 2

Preparing of Compound 59

Compound 59 was prepared in the same manner as in Synthesis Example 1, except that the intermediate B was used instead of the intermediate A. (Yield: 95%.)

$^1$H NMR ($CD_2Cl_2$, 300 MHz) δ (ppm) 6.96-6.85 (m, 22H), 6.78 (d, 14H), 2.25 (s, 30H); $^{13}$C NMR ($CD_2Cl_2$, 100 MHz) δ (ppm) 148.7, 145.9, 140.6, 134.4, 131.4, 130.3, 125.1, 122.3, 20.7, 14.4

The compound 59 produced through the above mentioned process was diluted in $CHCl_3$ to 0.2 mM, and UV spectrum of the diluted solution was obtained. In the UV spectrum, the maximum peaks appeared at 228.5 nm and 297 nm (FIG. 5).

Figure 6:
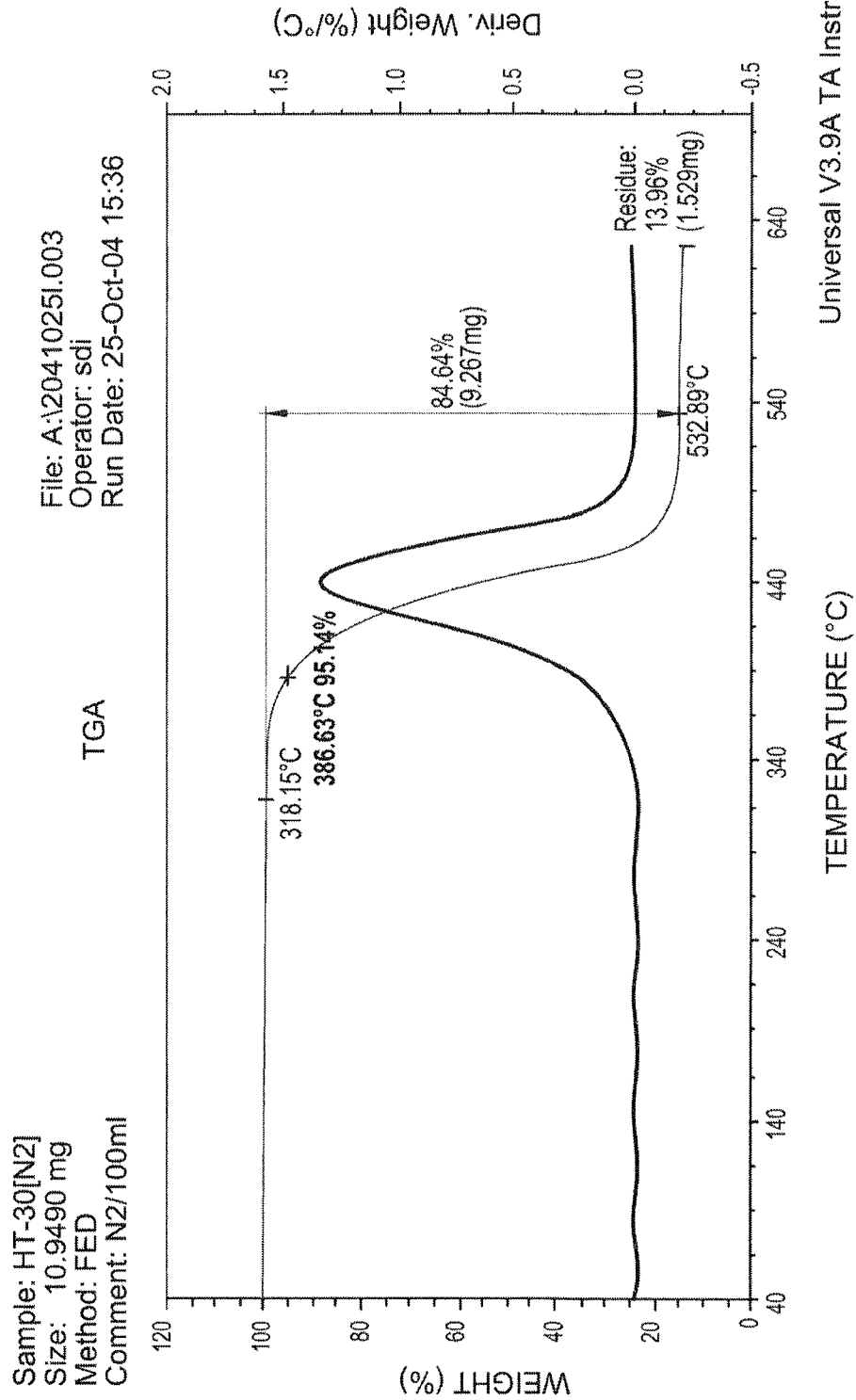
FIGS. 6 and 7 show results of TGA and DSC of Compound 59 prepared according to an embodiment of the present invention, respectively.
Figure 7:
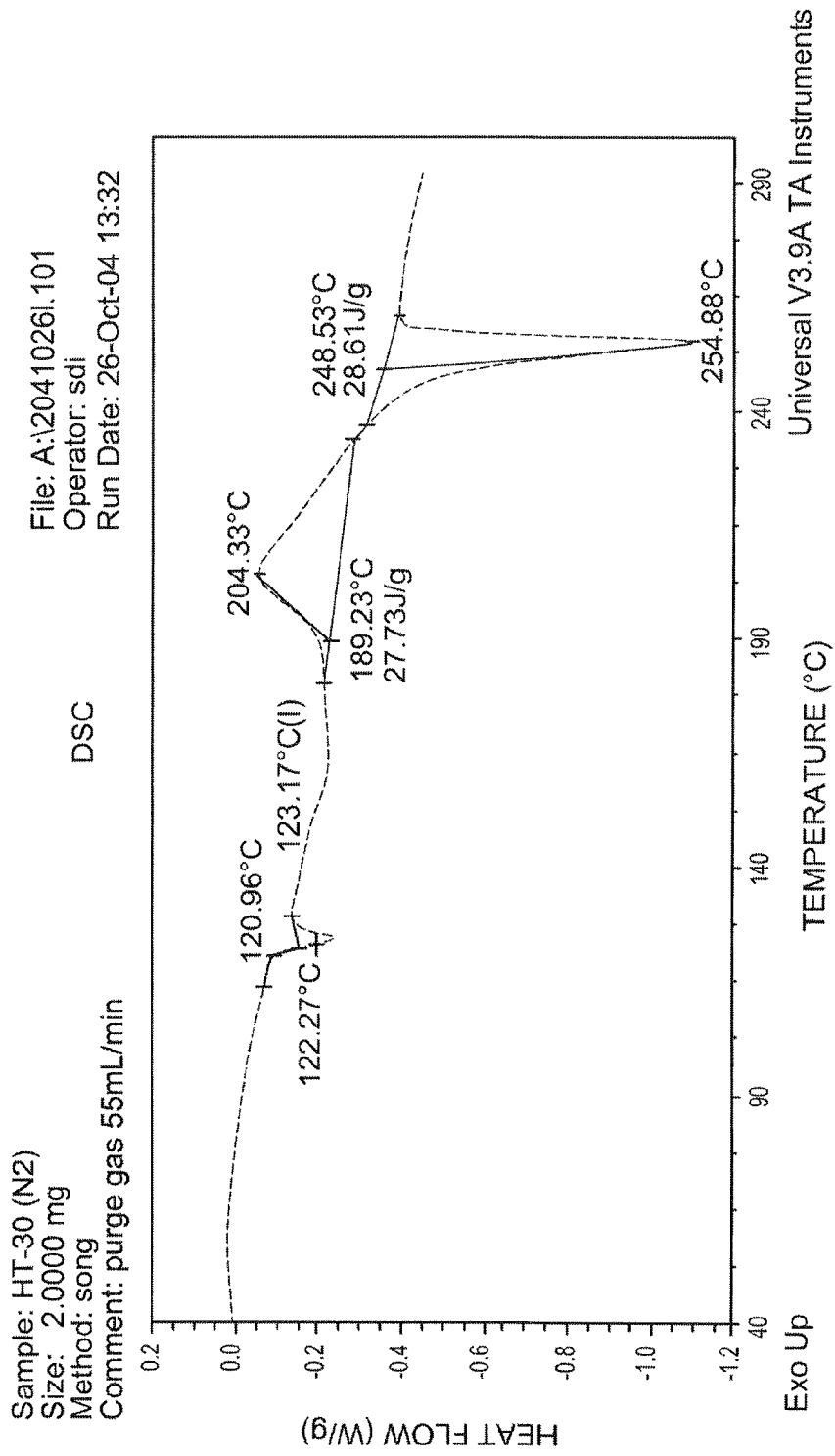

In addition, the compound 59 was thermally measured through TGA and DSC. TGA was performed using a Pt pan in disposable Al pan in a $N_2$ atmosphere while a temperature was increased by 10° C. per minute in a temperature range of room temperature to 600° C. DSC was performed using disposable Al pan in a $N_2$ atmosphere in a temperature range of room temperature to 400° C. As a result of such thermal analysis, Td was 387° C., Tg was 122° C., Tc was 204° C., and Tm was 255° C. (FIGS. 6 and 7.)

HOMO energy band and LUMO of the compound 59 were measured using an UV absorption spectrum and AC-2 that is an ionization potential measuring device. As a result, the HOMO and LUMO energy bands of the compound 59 were 5.35 eV and 2.24 eV, respectively.

Example 1

An ITO electrode, which acts as an anode, deposited on a glass substrate (produced from Corning Inc, surface resistance of 15 Ω/cm², thickness of 1200 Å) was cut to a size of 50 mm×50 mm×0.7 mm. The prepared glass substrate was ultrasonically cleaned in isopropyl alcohol for 5 minutes, ultrasonically cleaned in pure water for 5 minutes, cleaned using ultraviolet (UV) rays for 30 minutes, and then cleaned using ozone. The resulting glass substrate was installed on a vacuum deposition device.

IDE406 was deposited on the glass substrate to form a hole injection layer having a thickness of 600 Å. Subsequently, the compound 2 was vacuum deposited to form a hole transport layer having a thickness of 300 Å.

Alq₃ as a green fluorescent host and C545T as a green fluorescent dopant with a weight ratio of 98:2 were deposited on the hole transport layer to form an emission layer having a thickness of 200 Å. Then, Alq₃ was deposited to form an electron transport layer having a thickness of 300 Å, and LiF was deposited on the electron transport layer to form an electron injection layer having a thickness of 10 Å, and Al was vacuum deposited to form a cathode having a thickness of 3000 Å, thereby forming an LiF/Al electrode. As a result, an organic light emitting device was completely manufactured.

Comparative Example 1

An organic light emitting device was manufactured in the same manner as in Example 1, except that a hole transport layer was formed of NPB instead of the compound 2.

Turn-on voltages, current densities, luminance, and luminous efficiencies of organic light emitting devices prepared in Example 1 and Comparative Example 1 were measured.

As a result, the organic light emitting device prepared according to Example 1 had a turn-on voltage of 2.5 V; and exhibited the current density of 32.77 mA/cm², luminance of 4247 cd/m², the color coordinate of (0.31, 0.64), and the luminous efficiency of 12.96 cd/A when provided with 6.0 V. The organic light emitting device prepared according to Comparative Example 1 had a turn-on voltage of 3.0 V; and exhibited the current density of 7.76 mA/cm², luminance of 905.5 cd/m², the color coordinate of (0.30, 0.64), and the luminous efficiency of 11.56 cd/A when provided with 6.0 V.

Figure 8:
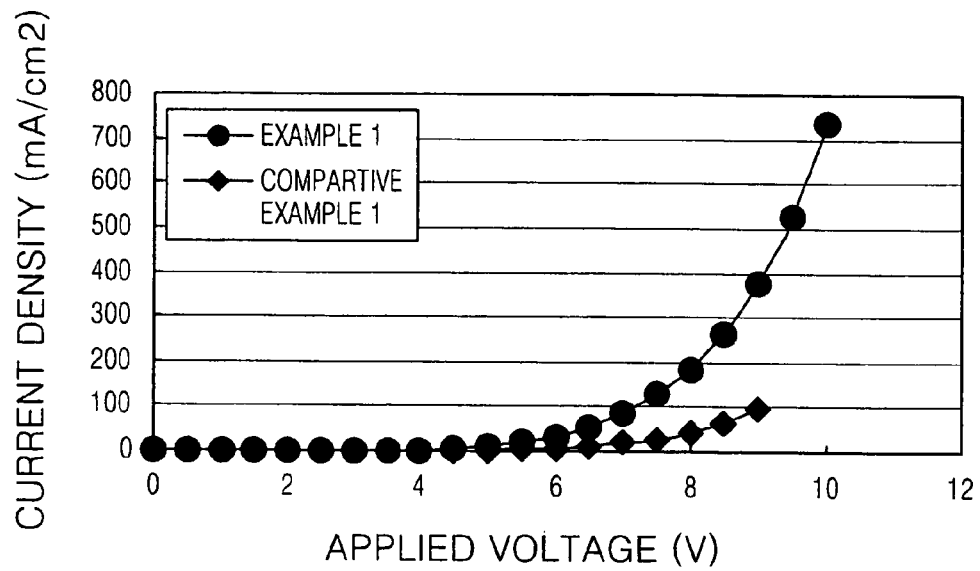
FIG. 8 is a graph of current density with respect to voltage of organic light emitting devices prepared in Example 1 and Comparative Example 1.
Figure 9:
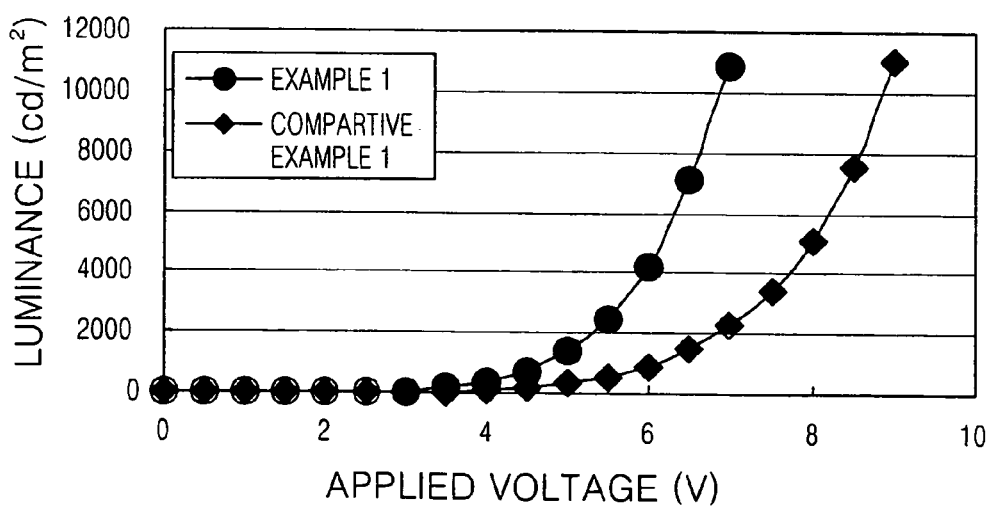
FIG. 9 is a graph of luminance with respect to voltage of organic light emitting devices prepared in Example 1 and Comparative Example 1.

As described above, the hole transport layer containing the compound 2 according to the present invention exhibited a better hole injecting or transporting capability than the hole transport layer containing NPB, and thus the turn-on voltage of the organic light emitting device prepared according to Example 1 decreased by 0.5 V. In addition, the organic light emitting device prepared according to Example 1 can obtain the same current density with a much lower voltage. Furthermore, luminance was increased due to an increase in the current density. FIGS. 8 and 9 are graphs of current density and luminance with respect to voltage of the organic light emitting devices prepared according to Example 1 and Comparative Example 1. Referring to FIGS. 8 and 9, the organic light emitting device prepared according to Example 1 exhibited better current density and luminance than the organic light emitting device prepared according to Comparative Example 1.

Figure 10:
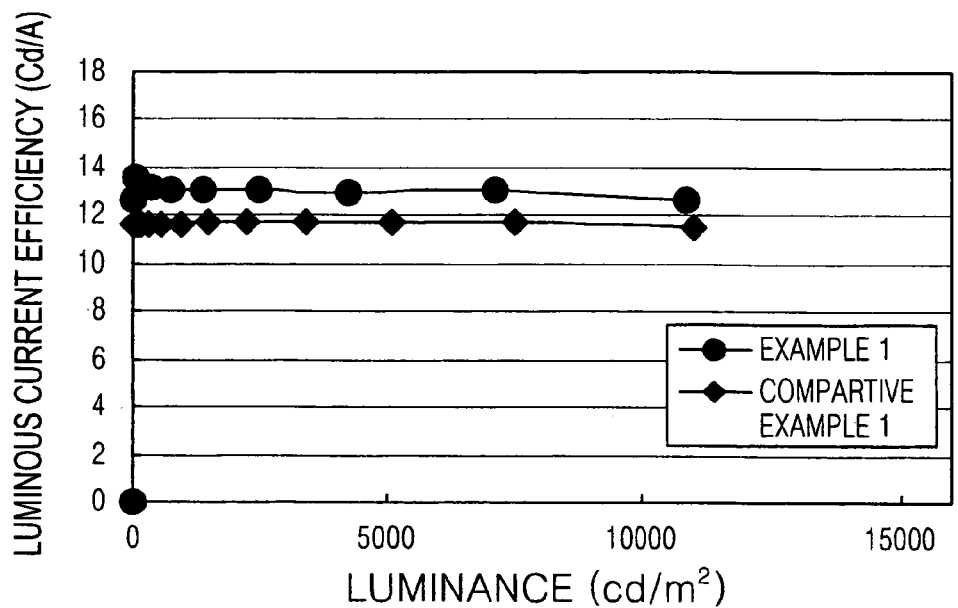
FIG. 10 is a graph of luminous current efficiency with respect to luminance of organic light emitting devices prepared in Example 1 and Comparative Example 1.
Figure 11:
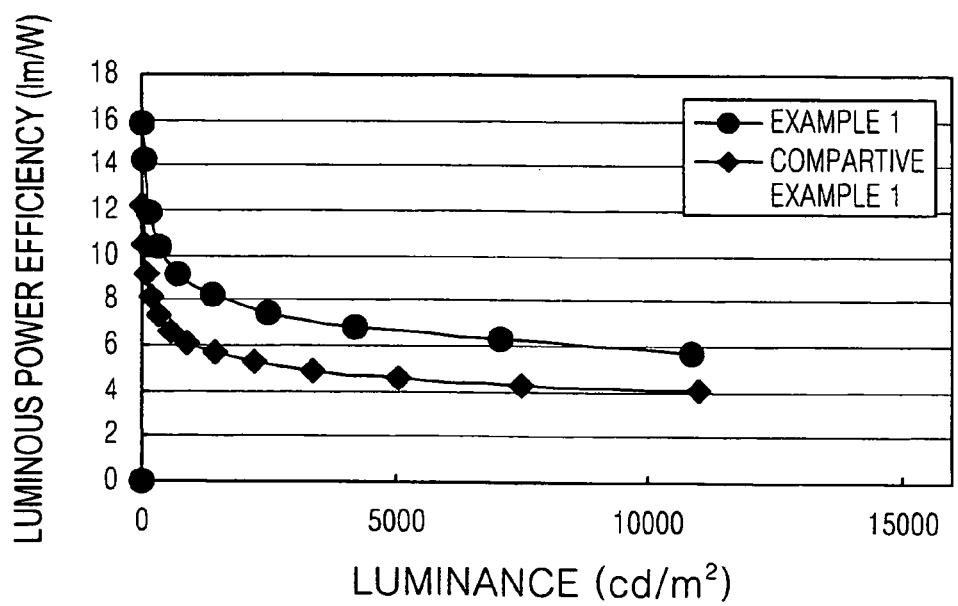
FIG. 11 is a graph of luminous power efficiency with respect to luminance of organic light emitting devices prepared in Example 1 and Comparative Example 1.

Referring to FIGS. 10 and 11, the organic light emitting device prepared according to Example 1 exhibited better current efficiency and electric power efficiency than the organic light emitting device prepared according to Comparative Example 1.

As described above, a triarylamine-based compound of formula 1 can be used as a hole injecting or hole transporting material suitable for a fluorescent or phosphorescent device emitting all colors including red, green, blue, white, etc., due to its excellent electrical properties and charge transporting capability. An organic light emitting device including an organic layer formed of the triarylamine-based compound exhibits high efficiency, a low operating voltage, high luminance, and a long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. An organic light emitting device, comprising:
a first electrode;
a second electrode; and
an organic layer interposed between the first electrode and the second electrode, the organic layer comprising a triarylamine-based compound represented by one of formulae 2-4:

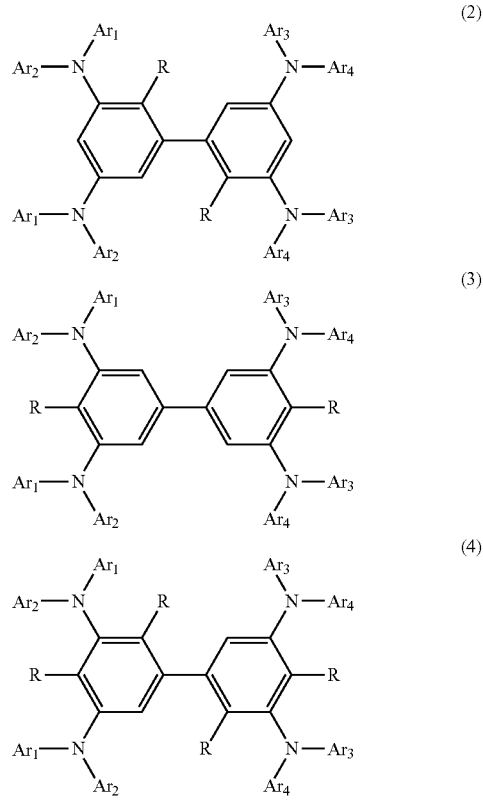

where Ar₁ through Ar₄ are independently a substituted or unsubstituted C6-C30 aryl group or a substituted or unsubstituted C2-C30 heterocyclic group; and
each R is independently a C1-C30 alkyl group.

2. The organic light emitting device of claim 1, wherein the organic layer is at least one selected from the group consisting of a hole injection layer, a hole transport layer, and an emission layer.

3. The organic light emitting device of claim 1, wherein the organic layer comprises a layer having hole injecting and hole transporting capabilities.

4. A method of preparing a triarylamine-based compound of one of formulae 2-4:

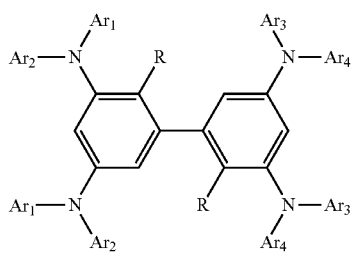
(2)

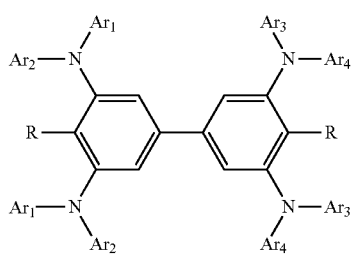
(3)

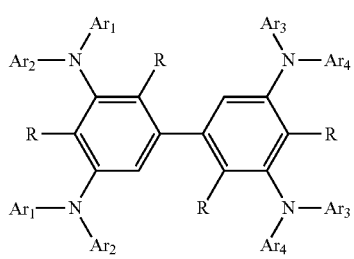
(4)

where $Ar_1$ through $Ar_4$ are independently a substituted or unsubstituted C6-C30 aryl group or a substituted or unsubstituted C2-C30 heterocyclic group; and each R is independently a C1-C30 alkyl group, the method comprising:

reacting compounds of formulae 8 through 10:

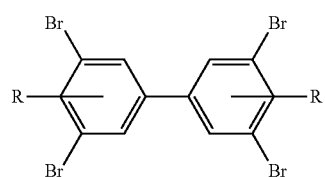
(8)

(9)

(10)

where $Ar_1$ through $Ar_4$ are independently a substituted or unsubstituted C6-C30 aryl group or a substituted or unsubstituted C2-C30 heterocyclic group; and each R is independently a C1-C30 alkyl group.

5. The method of claim 4, wherein the reaction is performed in the presence of tri(dibenzylideneacetone)dipalladium(0) at a reaction temperature of 50 to 150° C.

6. The method of claim 4, wherein the compound of formula 8 is prepared by reacting a compound of formula 11 with butyl lithium and then by reacting the resultant product with copper chloride:

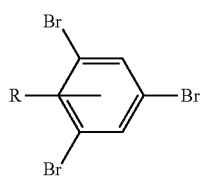
(11)

where R is a C1-C30 alkyl group.

7. The method of claim 6, wherein the reaction temperature for the preparation of the compound of formula 8 is in the range of −78° C. to 0° C.

8. An organic light emitting device, comprising:
a first electrode;
a second electrode; and
an organic layer interposed between the first electrode and the second electrode, the organic layer comprising a triarylamine-based compound prepared by the method of claim 4.

9. The organic light emitting device of claim 8, wherein the reacting of the compounds of formulae 8 through 10 is performed in the presence of tri(dibenzylideneacetone)dipalladium(0) at a reaction temperature of 50° C. to 150° C.

10. The organic light emitting device of claim 8, wherein the compound of formula 8 is prepared by reacting a compound of formula 11 with butyl lithium and then by reacting the resultant product with copper chloride:

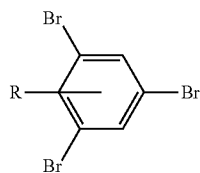
(11)

where R is a C1-C30 alkyl group.

11. The organic light emitting device of claim 10, wherein the reaction temperature for the preparation of the compound of formula 8 is in the range of −78° C. to 0° C.

12. The organic light emitting device of claim 1, wherein the triarylamine-based compound is represented by formula 2:

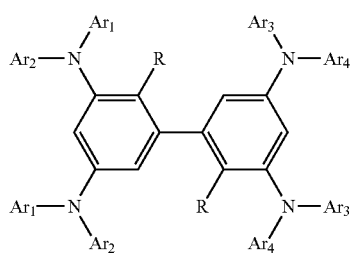

(2)

where Ar₁ through Ar₄ are as described in claim 14, and R is a C1-C10 alkyl group.

13. The organic light emitting device of claim 1, wherein the triarylamine-based compound is represented by formula 3:

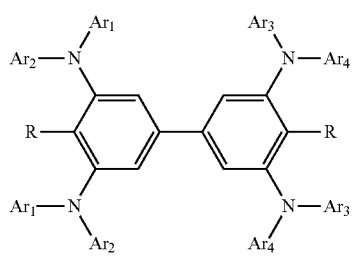

(3)

where each of Ar₁ through Ar₄ is as described in claim 14, and R is a C1-C10 alkyl group.

14. The organic light emitting device of claim 1, wherein the triarylamine-based compound is represented by formula 4:

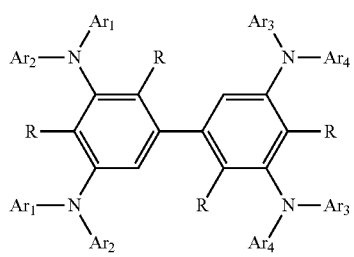

(4)

where each of Ar₁ through Ar₄ is as described in claim 14, and R is a C1-C10 alkyl group.

15. The organic light emitting device of claim 1, wherein the triarylamine-based compound is selected from the group consisting of the compounds represented by formulae below:

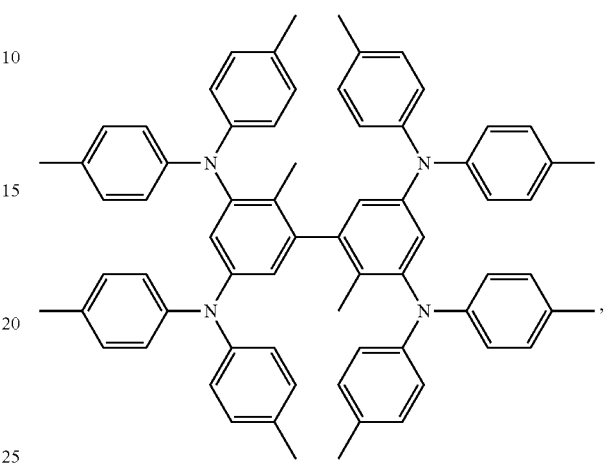

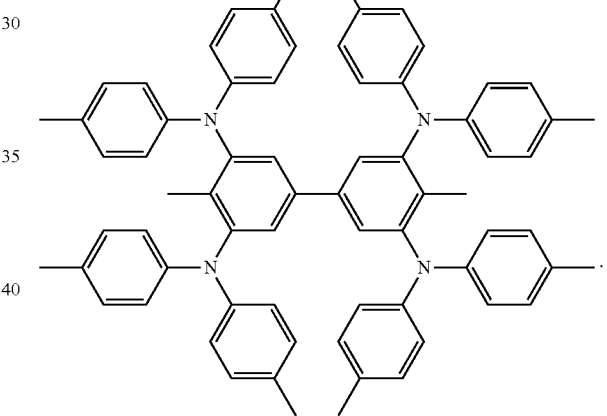

\* \* \* \* \*